United States Patent
Piérdet et al.

[11] 3,988,356
[45] Oct. 26, 1976

[54] NOVEL HAPTENES AND ANTIGENS
[75] Inventors: André Piérdet, Noisy-le-Sec; Michel Vignau, Neuilly-sur-Seine, both of France
[73] Assignee: Roussel-UCLAF, Paris, France
[22] Filed: July 7, 1975
[21] Appl. No.: 593,268

[30] Foreign Application Priority Data
July 10, 1974 France .............................. 74.23937

[52] U.S. Cl. ........................... 260/397.1; 260/397.45
[51] Int. Cl.² ........................... C07J 9/00; C07J 5/00
[58] Field of Search .................... 260/397.45, 397.1

[56] References Cited
UNITED STATES PATENTS
3,922,292  11/1975  Torelli et al. ..................... 260/397.1

Primary Examiner—Elbert L. Roberts
Attorney, Agent, or Firm—Hammond & Littell

[57] ABSTRACT
Novel haptenes of the formula

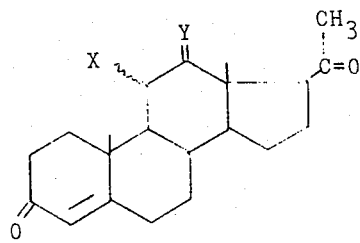

wherein when X is hydrogen, Y is =N-O-$(CH_2)_a$—COOH and a is a whole number of 1 to 12 and when

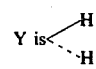

X is hemiterephthaloyloxy in the α- or β-position and antigens prepared therefrom by condensation with beef serum albumin.

8 Claims, No Drawings

NOVEL HAPTENES AND ANTIGENS

STATE OF THE ART

Experientia, Vol. 29 (5) (1973), p. 636-7 describes progesterone derivatives with a 11α-hemisuccinoyl group and French Medical Pat. No. 6234 describes a progesterone derivative with an =NOH group in the 12-position.

OBJECTS OF THE INVENTION

It is an object of the invention to provide the novel haptenes of formula I.

It is another object of the invention to provide a novel process for the preparation of haptenes of formula I.

It is an additional object of the invention to provide novel antigens derived from haptenes of formula I and beef serum albumin.

These and other objects and advantages of the invention will become obvious from the following detailed description.

THE INVENTION

The novel haptenes of the invention have the formula

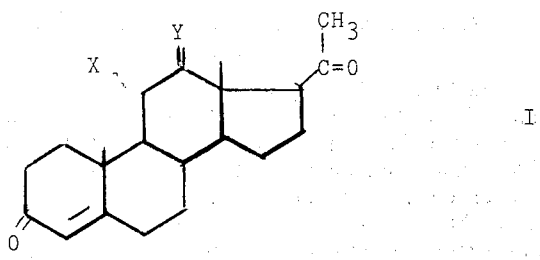

I wherein when X is hydrogen, Y is =N-O)-(CH$_2$)$_a$-COOH and a is a whole number of 1 to 12 and when

X is hemiterephthaloyloxy in the α- or β-position.

The group —(CH$_2$)$_a$-COOH is preferably derived from an aliphatic carboxylic acid of 2 to 5 carbon atoms such as acetic acid, propionic acid, butyric acid or pentylic acid. Among the compounds of formula I when X is hydrogen and Y is =N-O-(CH$_2$)$_a$-COOH, the preferred compound is 12-carboxymethoxyimino-Δ$^4$-pregnene-3,20-dione. Other preferred compounds are 11α- or 11β-hemiterephthaloyloxy-Δ$^4$-pregnene-3,20-dione.

The novel process of the invention for the preparation of haptenes of formula I wherein X is hydrogen and Y is =N-O-(CH$_2$)$_a$-COOH comprises reacting Δ$^4$-pregnene-3,12,20-trione with a compound of the formula H$_2$-N-O-(CH$_2$)$_a$- COOH   II to obtain the desired compound of formula I. The compound of formula II is preferably used in the form of its acid addition salts such as its hydrochloride. Δ$^4$-pregnene-3,12,20-trione may be prepared by the process described in Chem. Pharm. Bull., Vol. 12 (8) (1964), p. 859–865.

The process of the invention for the preparation of haptenes of formula I wherein

and X is hemiterephthaloyloxy in the α- or β-position comprises reacting Δ$^4$-pregnene-11ξ-ol-3,20-dione when ξ indicates the α- or β-position with a p-alkoxycarbonyl benzoic acid anhydride of the formula

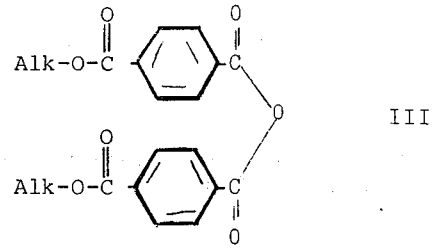

III wherein Alk is an alkyl of 1 to 6 carbon atoms to obtain a compound of the formula

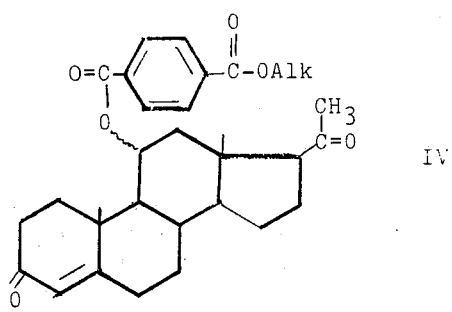

IV which is then saponified to obtain the corresponding 11α- or 11β-compound of formula I.

The p-alkoxycarbonyl benzoic acid anhydride of formula III is preferably p-methoxycarbonyl benzoic acid anhydride or p-ethoxycarbonyl benzoic acid anhydride. The saponification agent is preferably an alkaline base like an alkali metal hydroxide such as sodium hydroxide or potassium hydroxide; alkali metal amides such as sodium amide; alkali metal lower alcoholates such as potassium tert.-butylate, or alkali metal acetylides such as lithium acetylide in ethylene diamine. The saponification is preferably effected in a lower alkanol such as methanol or ethanol.

In a modification of the process of the invention, for the preparation of 11β-hemiterephthaloyloxy-Δ$^4$-pregnene-3,20-dione, Δ$^4$-pregnene-3,11,20-trione is reacted with a ketalization agent to form a compound of the formula

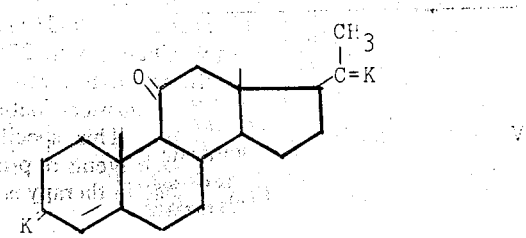

V wherein K is a ketone blocking group, reacting the latter with a reducing agent to form a compound of the formula

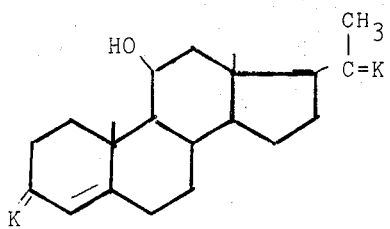

VI reacting the latter with a p-alkoxycarbonyl benzoic acid anhydride of formula III to obtain a compound of the formula

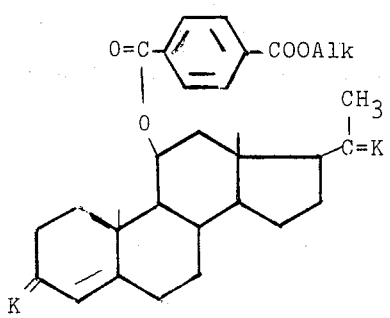

VII reacting the latter with a saponification agent to obtain the corresponding 11β-hemiterephthaloyloxy compound and subjecting the latter to acid hydrolysis to obtain the corresponding compound of formula I.

The blocking agents are preferably o-lower alkyl hydroxyamines such as o-methyldroxyamine or a lower alkanol or lower alkyleneglycol or dioxolane. The reducing agent is preferably an alkali metal borohydride such as sodium borohydride or lithium borohydride or potassium borohydride. The compound of formula III is preferably p-methoxycarbonyl-benzoic acid anhydride or p-ethoxycarbonyl-benzoic acid anhydride. The saponification agents are as above and the acid hydrolysis agent is preferably hydrochloric acid, sulfuric acid, acetic acid, citric acid or p-toluene sulfonic acid in one or more solvents such as lower alkanols like methanol, ethanol or isopropanol.

$\Delta^4$-pregnene-3,11,20-trione is known and may be prepared by the process of U.S. Pat. No. 2,403,683.

The novel process of the invention for the preparation of antigens comprises reacting a compound of formula I with an alkyl haloformate to obtain a mixed acid anhydride and reacting the latter with beef serum albumin to form the antigen. The alkyl haloformate is preferably isobutyl haloformate.

The antibodies which can be prepared from these antigens may be prepared by classical methods such as described by Erlanger /J. Biol. Chem., Vol. 228, p. 713/. The antibodies are specific to progesterone and this specificity is made evident by classical methods, notably by dialysis to equilibrium. This specificity makes the antibodies useful as dosage agents of progesterone and the interest of this dosage in therapy is well known.

In the following examples there are described several preferred embodiments to illustrate the invention and it is to be understood that the invention is not intended to be limited to the specific embodiments.

EXAMPLE 1

12-carboxymethoxyimino-$\Delta^4$-pregnene-3,20-dione 2.3 g of $\Delta^4$-pregnene-3,12,20-trione were added with stirring under a nitrogen current to 58 ml of ethanol and after heating the resulting solution to reflux, a solution of 765 g of the hemihydrochloride of aminooxyacetic acid, 7 ml of N sodium hydroxide solution and 58 ml of ethanol was added thereto over 6 ¾ hours. The stirring was maintained for 1 hour and the solution was concentrated. Water and acetic acid were added and the mixture was extracted with methylene chloride. The organic extracts were washed with water, dried and evaporated to dryness. The residue was chromatographed over silica gel and was eluted with a 50—50-0.2 mixture of benzene-ethyl acetate acid to obtain 12-carboxymethoxyimino-$\Delta^4$-pregnene-3,20-dione which after crystallation melted at 192° C.

EXAMPLE 2

11α-hemiterephthaloyloxy-$\Delta^4$-pregnene-3,20-dione

STEP A:

11α-(p-methoxycarbonylbenzoyloxy)-$\Delta^4$-pregnene-3,20-dione

A mixture of 1.652 g of $\Delta^4$-pregnene-11α-ol-3,20-dione, 2.500 g of p-methoxycarbonyl benzoic acid anhydride and 5 ml of pyridine were heated at 100°–105° C for 3 hours and the resulting solution was poured into a water-ice bath. The mixture was extracted with methylene chloride and the organic extracts were washed with water and evaporated to dryness under reduced pressure to obtain 3.050 g of product. The product chromatographed over silica gel and was eluted with a 5-5 mixture of benzene-ethyl acetate to obtain 2 g of 11α-(p-methoxycarbonylbenzoyloxy)-$\Delta^4$-pregnene-3,20-dione melting at 190° C.

STEP B:

11α-heimiterephthaloyloxy-$\Delta^4$-pregnene-3,20-dione

A few drops of methylene chloride were added to a solution of 0.098 g of the product of Step A in 5 ml of ethanol and then 0.37 ml of N sodium hydroxide solution were added. The mixture was stirred for 2 hours and then 10 drops of water were added after which the mixture was stirred for another hour. The mixture was acidified with acetic acid to just decoloration and was then poured into an ice-water bath. The mixture was extracted with methylene chloride and the extracts were washed with water and evaporated to dryness to obtain 0.109 g of product which was crystallized from a methylene chloride-isopropyl ether mixture to obtain 11α-hemiterephthaloyloxy-$\Delta^4$-pregnene-3,20-dione as an amorphous solid melting at about 220° C.

EXAMPLE 3

11β-hemiterephthaloyloxy-$\Delta^4$-pregnene-3,20-dione

STEP A: 3,20-bis-methyloxime-$\Delta^4$-pregnene-11-one 7.2 g of anhydrous sodium acetate and 6.52 g of o-methylhydroxylamine hydrochloride were added to a stirred mixture of 6.56 g of $\Delta^4$-pregnene-3,11,20-trione in 50 ml of methanol and the mixture was stirred at room temperature for 18 hours after which it was poured into 500 ml of water. The mixture was vacuum filtered, washed with water and dried to obtain 7.58 g of 3,20-bis-methyloxime-Δ⁴-pregnene-11-one melting at 140° C.

STEP B: 3,20-bis-methyloxime-Δ⁴-pregnene-11β-ol 1.8 g of potassium borohydride were added to a stirred mixture of 5.7 g of the product of Step A in solution in 60 ml of tetrahydrofuran, 30 ml of water and 3 ml of 0.1N sodium hydroxide solution and the mixture was stirred at 45° ± 2° C for 18 hours. Then, 0.9 g of potassium borohydride were added thereto and the mixture was stirred for another 5 hours at 45° C ± 2°. The mixture was cooled to room temperature and 5.5 ml of an aqueous 50% acetic acid solution were added and the mixture was concentrated. A mixture ice-water was added and the mixture was stirred for 30 minutes. The formed precipitate was vacuum filtered, washed and dried to obtain 5.4 g of a white powder. The product was chromatographed over silica gel and was eluted with an 85–15 mixture of benzene-ethyl acetate to obtain 4 g of 3,20-bis-methyloxime-Δ⁴-pregnene-11β-ol [isomer E in the 3 position] with an Rf = 0.37 and melting at 184° C and 0.6 g of 3,20-bis-methyloxime-Δ⁴-pregnene-11β-ol [Z isomer in 3 position] with an Rf = 0.20 and melting at 158° C.

STEP C:
3,20-bis-methyloxime-11β-(p-methoxycarbonylbenzoyloxy)-Δ⁴-pregnene (form E)

8.4 g of p-methoxycarbonyl benzoic acid anhydride, 4.1 ml of triethylamine and 2.9 g of 4-dimethylpyridine were added to a stirred mixture of 2.8 g of the E isomer of Step B in 82 ml of methylene chloride and the mixture was refluxed for 70 hours. 300 ml of benzene were added followed by the slow addition of potassium bisulfate until the pH was 1 to 2. The organic phase was washed with water, a sodium bicarbonate solution and then with water until the wash waters were neutral, dried and evaporated to dryness to obtain 6.99 g of a product. The product was chromatographed over silica gel and was eluted with a 90–10 benzene-ethyl acetate mixture to obtain a more mobile product which was crystallized from ethyl acetate to obtain the E isomer of 3,20-bis-methyloxime-11β-(p-methoxycarbonylbenzoyloxy)-Δ⁴-pregnene melting at 90° C.

STEP D:
3,20-bis-methyloxime-11β-hemiterephthaloyloxy-Δ⁴-pregnene (form E)

4 ml of an aqueous 0.5 N sodium hydroxide solution were added dropwise with cooling to 168 mg of the product of Step C in 4 ml of ethanol and 8 ml of aqueous ethanol were added thereto with stirring over about 30 minutes. Stirring was continued until dissolution was practically complete and after the addition of 60 ml of water, the mixture was extracted with ether. The aqueous phase was filtered and the pH was adjusted to 1–2. The mixture was vacuum filtered and the recovered precipitate was washed with water and dried to obtain 139 mg of product which was crystallized from ethyl acetate to obtain the E isomer of 3,20-bis-methyloxime-11β-hemiterephthaloxy-Δ⁴-pregnene melting at 250° C.

STEP E:
11β-hemiterephthaloyloxy-Δ⁴-pregnene-3,20-dione

A mixture of 88 mg of the product of Step D in 8 ml of acetone and 8 ml of 2N hydrochloric acid was stirred until hydrolysis was complete and the acetone was separated. The mixture was filtered to obtain 50 mg of 11β-hemiterephthaloyloxy-Δ⁴-pregnene-3,20-dione melting at 180° C.

EXAMPLE 4

Beef serum albumin reaction 0.12 ml of tri-n-butylamine and 0.063 ml of isobutyl orthoformate were added at 12°–14° C with stirring under a nitrogen current to a mixture of 201 mg of 12-carboxymethoxyimino-Δ⁴-pregnene-3,20-dione in 5 ml of dioxane and the solution was stirred for 20 minutes to obtain a solution of the mixed acid anhydride of 12-carboxymethoxyimino-Δ⁴-pregnene-3,20-dione.
690 mg of beef serum albumin were added at 0 to 5° C with stirring under a nitrogen atmosphere to 18 ml of water and 2 ml of dioxane and the reaction mixture was stirred at 0° to 5° C until dissolution was complete.

16 ml of dioxane cooled to 12° to 14° C were added to the beef serum albumin solution and then 0.69 ml of N sodium hydroxide solution were added thereto followed by the acid anhydride solution and then 2 ml of dioxane. The solution was stirred at 0° to 5° C for 1 hour and 0.33 ml of N sodium hydroxide were added. The solution was stirred at 0° to 5° C under a nitrogen atmosphere and was then subjected to dialysis through a membrane at 0° to 5° C for 20 hours. The solution was acidified to a pH of 4 by addition of N hydrochloric acid and the mixture stood overnight at −18° C. The ice obtained was allowed to slowly melt and the supernatant solution was decanted off. The precipitate was dissolved in 50 ml of an aqueous iced solution containing 1% of sodium bicarbonate. The solution was subjected to a second dialysis through a membrane for 24 hours and the dialyzate was extracted with chloroform. The aqueous phase was lyophilized to obtain 759 mg of beef serum albumin condensed with 12-carboxymethoxyimino-Δ⁴-pregnene-3,20-dione.

Various modifications of the products and process of the invention may be made without departing from the spirit or scope thereof and it should be understood that the invention is intended to be limited only as defined in the appended claims.

We claim:
1. An haptene of the formula

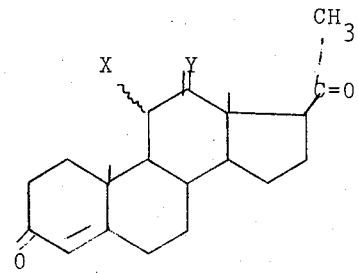

wherein when X is hydrogen, Y is =N-O-(CH₂)ₐ-COOH and a is a whole number of 1 to 12 and when

X is hemiterephthaloyloxy in the α- or β-position.

2. A compound of claim 1 wherein X is hydrogen and Y is =N-O-(CH₂)ₐ-COOH.

3. A compound of claim 2 wherein a is 1 to 4.

4. A compound of claim 1 which is 11β-hemiterephthaloyloxy-Δ⁴-pregnene-3,20-dione.

5. A compound of claim 1 which is 11α-hemiterephthaloyloxy-Δ⁴-pregnene-3,20-dione.

6. A compound of claim 1 which is 12-carboxymethoxyimino-Δ⁴-pregnene-3,20-dione.

7. A process for the preparation of a compound of claim 1 wherein

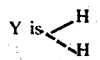

and X is hemiterephthaloyloxy in the α- or β-position comprises reacting Δ⁴-pregnene-11ξ-ol-3,20-dione wherein ξ indicates the α-or β-position with a p-alkoxycarbonyl benzoic acid anhydride of the formula

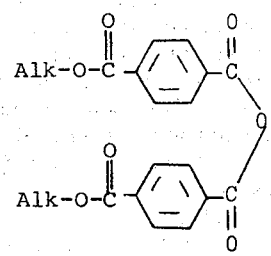

wherein Alk is an alkyl of 1 to 6 carbon atoms to obtain a compound of the formula

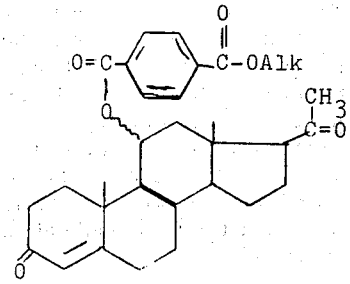

which is then saponified to obtain the corresponding 11α- or 11β-compound of claim 1.

8. A process for the preparation of the compound of claim 4 comprising reacting Δ⁴-pregnene-3,11,20-trione with a ketalization agent selected from the group consisting of o-lower alkyl hydroxylamine, lower alkanol, lower alkyleneglycol, and dioxolane to form a compound of the formula

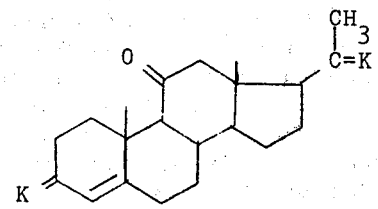

wherein K is a ketone blocking group, reacting the latter with an alkali metal borohydride to form a compound of the formula

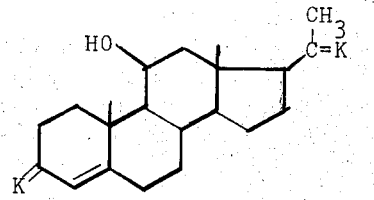

reacting the latter with a p-alkoxycarbonyl benzoic acid anhydride of formula III to obtain a compound of the formula

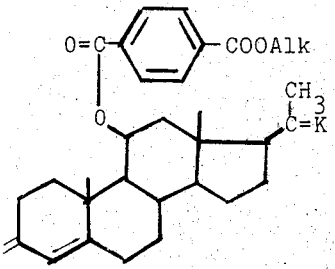

reacting the latter with a saponification agent to obtain corresponding 11β-hemiterephthaloyloxy compound and subjecting the latter to acid hydrolysis to obtain the corresponding compound of claim 4.

* * * * *